United States Patent
Smallridge et al.

(10) Patent No.: US 6,271,008 B1
(45) Date of Patent: Aug. 7, 2001

(54) YEAST-BASED PROCESS FOR PRODUCTION OF L-PAC

(75) Inventors: Andrew John Smallridge; Maurice Arthur Trewhella; Margaret Mary Del Guidice, all of Footscray (AU)

(73) Assignees: Victoria University of Technology; Polychip Pharmaceuticals PTY LTD, both of Victoria (AU)

( * ) Notice: Subject to any disclaimer, the term of this patent is extended or adjusted under 35 U.S.C. 154(b) by 0 days.

(21) Appl. No.: 09/701,704

(22) PCT Filed: Jun. 3, 1999

(86) PCT No.: PCT/AU99/00433
§ 371 Date: Feb. 2, 2001
§ 102(e) Date: Feb. 2, 2001

(87) PCT Pub. No.: WO99/63103
PCT Pub. Date: Dec. 9, 1999

(30) Foreign Application Priority Data

Jun. 3, 1998 (AU) .................................................. PP 3882

(51) Int. Cl.[7] ................. C12P 7/26; C12P 7/28
(52) U.S. Cl. .......................... 435/148; 435/150; 435/156; 435/942
(58) Field of Search .................................. 435/148, 150, 435/156, 942

(56) References Cited

U.S. PATENT DOCUMENTS 5,173,413   12/1992   Coughlin et al. .

FOREIGN PATENT DOCUMENTS

90/04639    5/1990   (WO) .

OTHER PUBLICATIONS

P. Nikolova et al., "Whole cell yeast biotransformations in two–phase systems: effect of solvent on product formation and cell structure", *Journal of Industrial Microbiiology*, 10:169–177 (1992).

M. Takemoto et al., "Synthesis of optically active α–phenylpyridylmethanols with Baker's Yeast", *Chem. Pharm. Bull.*, 42:802–805 (1994).

*Primary Examiner*—Herbert J. Lilling
(74) *Attorney, Agent, or Firm*—Fulbright & Jaworski, LLP

(57) ABSTRACT

This invention relates to yeast-mediated catalysis in organic solvents, and in particular the yeast-mediated condensation between pyruvate and a substituted aromatic aldehyde to yield the corresponding acyloin (hydroxy ketone) compound. The invention provides a method of synthesis of a substituted carbinol compound, comprising the step of subjecting the corresponding substituted aromatic aldehyde to acyloin condensation mediated by a yeast in an organic solvent under non-fermenting conditions. Preferably the yeast is *Saccharomyces cerevisiae*. In a preferred embodiment, the reaction is that between pyruvate and benzaldehyde to yield phenylacetylcarbinol, the precursor to ephedrine, to yield a product of high enantiomeric purity.

30 Claims, No Drawings

YEAST-BASED PROCESS FOR PRODUCTION OF L-PAC

This invention relates to organic compounds useful as precursors for the synthesis of a-variety of products, particularly for synthesis of compounds useful as E pharmaceutical agents. The method of the invention utilises yeast-mediated catalysis in organic solvents, and in particular the yeast-mediated condensation between pyruvate and a substituted aromatic aldehyde to yield the corresponding acyloin (hydroxy ketone) compound. In a preferred embodiment, the reaction is that between pyruvate and benzaldehyde to yield phenylacetylcarbinol, the precursor to ephedrine, in high enantiomeric purity.

BACKGROUND OF THE INVENTION

Physicochemical methods for production of enantiomerically pure compounds usually involve multi-step synthesis incorporating one or more steps which are asymmetric, and laborious purification procedures. Such methods are not only tedious, but frequently provide relatively poor yields. Alternatively enantiomerically-pure starting materials can be used, together with enantioselective reaction steps; however, such pure starting materials are available only for a very limited number of desired compounds.

In an attempt to overcome the difficulties of using traditional organic chemical methods, biological systems have been intensively investigated. Such systems show a very high degree of stereoselectivity in their reactions, and therefore microbiological, enzymatic or chemoenzymatic reactions for achieving specific reaction steps with a variety of reagents have been attempted. For example, microorganisms of a number of genera have been proposed for synthesis of optically active α-substituted derivatives of 3-hydroxypropionic acid for use as intermediates in the synthesis of compounds such as α-tocopherol, muscones and pharmaceutical, insecticidal and agricultural chemical agents (U.S. Pat. No. 4,734,367 by Hoffman-La Roche, Inc.). Most such procedures use whole-cell fermentation systems in aqueous media, or isolated enzymes with a specific desired activity. However, fermentation systems present the disadvantage that purification of the desired product can be difficult, and yields tend to be low; while the yield and convenience of the reaction can be improved by utilising immobilised cells, or cells which have been selected or genetically modified, this adds significantly to the cost of the process. The use of purified enzymes is normally prohibitively expensive, and again without the use of immobilised enzyme the yield tends to be low and purification difficult.

In recent years, intense efforts have been directed towards development of methods which are highly selective, provide a good rate of transformation, and enable easy, non-chromatographic separation and purification of the product. It would be particularly desirable if reactions could be carried out in organic solvents, since these are particularly convenient for large scale reactions and purifications.

It has been shown that dry baker's yeast is able to effect non-fermentative reduction of a-keto esters in organic solvents such as hexane or benzene, to produce the corresponding α-hydroxy esters with good yield and selectivity (Nakamura et al, 1988; Nakamura et al, 1990; Nakamura et al, 1991; Nakamura et al, 1993); reduction of β-keto esters in petroleum ether, diethyl ether, toluene, carbon tetrachloride and petrol has also been demonstrated (Jayasinghe et al, 1993; Jayasinghe et al, 1994; North, 1996). Although initially it was thought that immobilisation of yeast, for example in polyurethane, was essential in order to maintain stability of cell membrane-bound coenzymes for the dehydrogenases and reductases which catalyse the reaction (Nakamura et al, 1988; Nakamura et al, 1990), it was subsequently found that the addition of a very small proportion of water to the organic system would avoid the need for immobilisation (Nakamura et al, 1991).

Ephedrine (α-[1-(methylamino)ethyl]benzene-methanol), originally isolated from plants of the genus Ephedra, occurs as the naturally-occurring isomers l-ephedrine and d-pseudoephedrine, and other pharmacologically active isomers include d-ephedrine and l-pseudoephedrine. These compounds are adrenergic sympathomimetic agents and have antihistamine activity; l-ephedrine is widely used as a bronchodilator, while d-pseudoephedrine is widely used as a decongestant. Compounds of these groups are present in a very wide range of prescription and over-the-counter pharmaceutical formulations.

The production of l-phenylacetylcarbinol, a precursor of l-ephedrine, by catalysis using whole baker's yeast cells in aqueous medium was one of the first microbial biotransformation processes to be used commercially (Neuberg and Hirsch, 1921; see also Hildebrandt and Klavehn, 1934). This reaction involves the yeast-induced condensation of benzaldehyde with acetyl-coenzyme A. The reaction has been widely investigated, and has been shown to be mediated by the enzyme pyruvate decarboxylase (Groger, Schmander and Mothes, 1966). It has also been shown that the reaction has a relatively broad specificity for the substrate, enabling a variety of substituted aromatic aldehydes to be converted to the corresponding substituted optically-active phenylacetylcarbinols (Long, James and Ward, 1989).

Although this yeast-catalysed system has been widely exploited, this has normally utilised aqueous systems, which are inconvenient for large-scale extraction and purification, which require organic solvents. Additionally, fermentation systems present the disadvantage that purification of the desired product can be difficult, and yields tend to be low; while the yield and convenience of the reaction can be improved by utilising immobilised cells, or cells which have been selected or genetically modified, this adds significantly to the cost of the process. The use of purified enzymes is normally prohibitively expensive, and again without the use of immobilised enzyme the yield tends to be low and purification difficult.

We have now surprisingly found that yeast-mediated acyloin condensation of benzaldehyde can be achieved in an organic solvent using non-fermenting yeast, and that addition of a small proportion of ethanol to the reaction mixture suppresses formation of undesired side-products. Even more surprisingly, by performing the reaction at reduced temperature, an even greater reduction of side-reactions can be achieved, without loss of catalytic activity. The effect of reduction in temperature appears to be generally applicable to both aqueous and non-aqueous systems utilising a non-fermenting yeast.

Although Ward and co-workers have carried out investigations using whole cell yeast biotransformation in two-phase organic systems with a water content of at least 10% (Nikolova and Ward, 1991; 1992a; 1992b; Ward, 1995), the yields of phenylacetylcarbinol were low, and the levels of side-products were unacceptably high.

The first description of the synthesis of l-ephedrine was contained in a patent by Hildebrandt and Klavehn (1934) and made use of the discovery by Neuburg and Hirsch (1921) that fermenting strains of Saccharomyces cerevisae in aqueous systems would convert benzaldehyde to phenylacetylcarbinol. The yield of the carbinol was typically about 18%, and significant amounts of both benzyl alcohol and benzoic acid were obtained as side-products.

In a preferred embodiment, yields of around 24% with the almost total absence of side-products were obtained using the method of the invention.

SUMMARY OF THE INVENTION

In a first aspect, the invention provides a method of synthesis of a carbinol compound, comprising the step of subjecting the corresponding aromatic aldehyde to acyloin condensation mediated by a yeast in an organic solvent under non-fermenting conditions, in the presence of an aliphatic alcohol or aliphatic aldehyde.

Any yeast capable of effecting reduction may be used. It is economically advantageous to use the cheapest yeast available, and ordinary baker's yeast, Saccharomryces cerevisiae, is preferred. Strains of yeast adapted to other purposes, including brewing yeast and wine or sherry yeasts could also be employed. Strains specifically adapted to an organic solvent environment or for enhanced reduction efficiency may be used; such strains include conventionally-selected and genetically modified strains. For maximum efficiency of reaction, it is advisable to present the maximum surface area of yeast for contact with the reactants. This can be effected by using "active" dried yeast, which is readily commercially available as "instant dry yeast", and may be stored at room temperature. Alternatively, well-pulverised dry baker's yeast may be used. Other yeasts, such as those described in U.S. Pat. No. 4,734,367, or fungi such as those disclosed in Chênevert et al (1992) may also be used. The person skilled in the art will readily be able to test whether any specific organism will function for the purposes of the invention, using the methods described herein.

Preferably the aliphatic alcohol or aliphatic aldehyde is ethanol or acetaldehyde, suitably 0.1 ml per g yeast. This results in a significant increase in the yield of carbinol, and reduces the amount of aromatic alcohols produced as a side-reaction. Ethanol is preferred, since this results in superior conversion of the aromatic aldehydes to the desired carbinol, and lower yield of undesired reduction product. Without wishing to be bound by any particular theory, it is believed that the ethanol or acetaldehyde provides an alternative substrate for the reductase enzymes thus inhibiting the formation o f side products such as benzyl alcohol. Therefore, it is predicted that other aliphatic alcohols or aliphatic aldehydes could perform the same function.

Although the reaction can be performed at ambient temperature, suitably 16–24° C., preferably 20° C., we have surprisingly found that significantly better results are obtained at lower temperatures, in the range 0–52° C. The reason for the improved performance and further reduction of side-reactions which is observed is not presently understood; however, we have observed that the activity of the yeast at these reduced temperatures is comparable to that at ambient temperature. This result is particularly surprising, because it would normally be expected that a yeast-mediated reaction would demonstrate a temperature optimum at ambient or slightly elevated temperature, although Shiu and Rogers (1996), have shown that isolated pyruvate decarboxylase, the enzyme involved in the acyloin condensation reaction, exhibits increased activity at 4° C.

The solvent may be any suitable organic solvent of low or moderate polarity, such as petroleum ether, carbon tetrachloride, hexane and other hydrocarbons, diethyl ether, toluene, or benzene. We have shown that reduction of ethyl acetoacetate (another yeast-mediated reaction) can be achieved in good yields and with high enantioselectivity in a range of mixed organic solvent systems, including 2-ethoxyethanol/diethyl ether, pyridine/carbon tetrachloride, chloroform/petroleum ether and ethyl acetate/toluene. We have found that petroleum ether is especially suitable, and has the advantage of low cost. We have found that in the yeast-mediated reduction of ethyl acetoacetate, baker's yeast retains its reducing a activity when 1 to 30% v/v of a polar solvent is added to a non-polar organic solvent, and this is also expected to be the case in the current invention, because the crucial factor in the choice of the solvent is whether the yeast remains active which is not dependent on the particular reaction concerned. Preferably 1 to 5% of polar solvent is added. The polar solvent is preferably chloroform, dichloromethane, methyl ethyl ketone, or methyl isobutyl ketone; the best results for mixed solvents were obtained with chloroform or dichloromethane in petroleum ether. In general, a single solvent is preferred.

It is known that in order to preserve functioning of an enzyme in an organic solvent environment it is necessary for the enzyme to be fully hydrated by being surrounded by a few layers of water molecules. This requirement is satisfied by providing a ratio of 0.6 to 1.2 ml water/g of yeast, preferably 1.0 ml water/g of yeast. This results in a single phase organic system as all of the water is absorbed into the yeast. A two-phase system reduces the yield of the product and makes isolation of the product considerably more difficult.

Once the yeast-mediated reaction has been completed, the yeast can readily be separated from the reaction mixture by filtration and washing. The reaction mixture, comprising product, unreacted starting material, solvent and minor impurities, is subjected to conventional purification, for example by flash distillation, to yield the purified product. Optionally the yeast can be extracted with an organic solvent such as ethyl acetate to yield a marginal amount of further product.

In a preferred embodiment, the invention provides a method for yeast-mediated conversion of benzaldehyde to phenylacetylcarbinol, according to the following reaction:

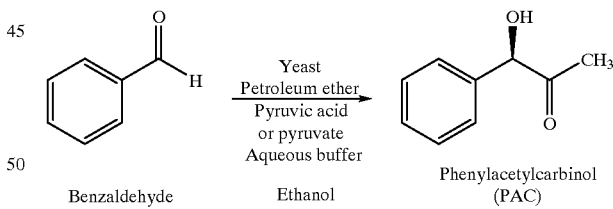

Benzaldehyde     Ethanol     Phenylacetylcarbinol (PAC)

It will be clearly understood that the benzaldehyde, the pyruvic acid, or both may optionally be substituted, and that pyruvate, for example sodium pyruvate, may be used as an alternative to pyruvic acid. However, preferably pyruvic acid is used, since the sodium pyruvate is more expensive, and we have found that one quarter as much pyruvic acid is required compared to pyruvate. Aromatic aldehydes substituted with alkyl, aryl, halo, nitro, hydroxy, alkoxy, amino, carbonyl, thioxy or thioalkoxy groups or composites of these groups may also be used instead of benzaldehyde.

For either sodium pyruvate or pyruvic acid, the pH of the pyruvate/citrate buffer solution is preferably between 5 and 6, more preferably pH 5.45. Between 0.6 and 1.2 ml buffer/g of yeast should preferably be used for optimal results.

While the ratio of yeast to substrate will vary depending on the individual system, and is readily determined experimentally using routine trial and error methods, we have found that for the conversion of benzaldehyde to phenylacetylcarbinol the optimum ratio is 5 g yeast/mmol benzaldehyde; increasing the amount of yeast results in only a small increase in conversion, and lower amounts of yeast provide lower conversion.

Similarly, the optimum reaction time may readily be determined, and for the benzaldehyde-phenylacetyl-carbinol system we have investigated reaction times from 12 to 72 hours, and have found that when the reaction is continued for longer than 24 hours there is very little improvement in conversion, and that there is an increase in production of by-products.

In a particularly preferred embodiment, production of undesired side-products is reduced by performing the catalysis reaction at below ambient temperature. Preferably the temperature is 0–5° C.

In a second aspect, the invention provides a method of synthesis of a substituted carbinol compound comprising the step of subjecting the corresponding substituted aromatic aldehyde to acyloin condensation mediated by a yeast in an organic solvent under non-fermenting conditions, in which the reaction mixture comprises water sufficient to activate the yeast but not to form a two phase system.

In a third aspect, the invention provides a method of synthesis of a substituted carbinol compound comprising the step of subjecting the corresponding substituted aromatic aldehyde to acyloin condensation mediated by a yeast in an organic solvent under non-fermenting conditions, in which the reaction is performed at 0–10° C.

For the purposes of this specification it will be clearly understood that the word comprising, means "including but not limited to", and that the word "comprises" has a corresponding meaning.

DETAILED DESCRIPTION OF THE INVENTION

The invention will now be described in detail by way of reference only to the following non-limiting examples.

EXAMPLE 1
Yeast-Mediated Acyloin Condensation of Benzaldehyde Using Pyruvic Acid Pyruvic acid buffer was prepared by dissolving pyruvic acid (10.44 g, 119 mmol) in 100 ml of 0.05 M sodium citrate. Ammonium acetate was added to give a pH of 5.45. Benzaldehyde (106 mg, 1 mmol), petroleum ether (80 ml), ethanol (0.5 ml), baker's yeast (5 g) and the pyruvic acid buffer (5 ml) were stirred at 50° C. for 24 h. The mixture was then filtered and the yeast washed with diethyl ether.

The combined organic layers were then washed with 10% sodium carbonate. After removal of the solvent in vacuo the product was purified by flash distillation (200° C./1 mm) to give phenylacetylcarbinol (30 mg, 20% yield). Gas chromatography (GC) of the product showed pure PAC (11.88 min.). Chiral GC showed a ratio of 95:5, 90% ee.

$[\alpha]_D$=−262.6 (c=0.745, $CHCl_3$). $^1H$ NMR ($CDCl_3$) δ 7.33–7.52, M, Ph; δ 5.12, s, CH; δ 2.06, s, $CH_3$.

EXAMPLE 2
Yeast-Mediated Acyloin Condensation of Benzaldehyde Using Sodium Pyruvate 9.5 ml of 0.1 M citric acid and 40.5 ml of 0.1 M tri-sodium citrate were diluted to 100 ml to give a pH 6 citrate buffer solution. (Ref.: Buffers for pH and Metal Ion Control, D. D. Perrin and B. Dempsey, Publ. John Wiley and Sons, pg 103).

Petroleum spirit (40 ml), ethanol (0.5 ml), the pH 6 citrate buffer (5 ml) and sodium pyruvate (2.5 g, 23 mmol) were stirred at room temperature for 1 h. Benzaldehyde (127 mg, 1.2 mmol) and baker's yeast (5 g) were then added and the reaction stirred at 5° C. for 24 h. The mixture was then filtered and yeast washed with diethyl ether. After removal of the solvent in vacuo the product was purified by flash distillation (200° C./1 mm) to give phenylacetylcarbinol (44 mg, 24%). The GC of the product showed pure PAC (11.88 min.). Chiral GC showed a ratio of 97.5:2.5, 95% ee.

$[\alpha]_D$=−375.8 (c=1.6, $CHCl_3$). $^1H$ NMR ($CDCL_3$) δ 7.33–7.52, M, Ph; δ 5.12, s, CH; δ 2.06, S, $CH_3$.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

It will be clearly understood that, although a number of prior art publications are referred to herein, this reference does not constitute an admission that any of these documents forms part of the common general knowledge in the, in Australia or in any other country.

REFERENCES

Chenevert, R. Fortier, G. and Rhlid, R. B. Tetrahedron, 1992 48 6769–6776

Csuk, R. and Glanzer, B. I. Chem. Rev., 1991 91 49–57

Groger, D., Schmander, H. P. and Mothes, K. Z. Allg. Mikrobol., 1966 6 275

Hildebrandt, G. and Klavehn, W. 1934 U.S. Pat. No. 1,956, 950

Hudlicky, T., Gillman, G. and Andersen, C. Tetrahedron Asymmetry, 1992 3 281

Jayasinghe, L. Y., Smallridge, A. J. and Trewhella, M. A. Tetrahedron Letters, 1993 34 3949

Jayasinghe, L. Y., Kodituwakku, D., Smallridge, A. J. and Trewhella, M. A. Bull. Chem. Soc. Jpn. 1994 67 2528

Kawai, A., Asano, T. and Imai, Y. Bull. Chem. Soc. Jpn., 1988 61 3014

Long, A., James, P. and Ward, O. P. Biotechnol. Bioeng., 1989 33 657–660

Nakamura, K., Inoue, K., Ushio, K., Oka, S. and Ohno, A. J. Org. Chem., 1988 53 2589–2593

Nakamura, K., Miyai, T., Inoue, K., Kawasaki, S., Oka, S. and Ohno, A. Biocatalysts, 1990 3 17–24

Nakamura, K., Kondo, S., Kawai, Y. and Ohno, A. Tetrahedron Letters, 1991 32 7075

Nakamura, K., Kondo, S., Kawai, Y. and Ohno, A. Bull. Chem. Soc. Jpn., 1993 66 2738

Neuberg, C. and Hirsch, J. Biochem. Z., 1921 115 282–310

Nikolova, P. and Ward O. P. Biotechnol. Bioeng., 1991 38 493–498

Nikolova, P. and Ward, O. P. J. Industrial Microbiology, 1992a 10 169–177

Nikolova, P. and Ward, O. P. Biocatalysis in Non-Conventional Media, edited by J. Tramper et al, 1992b Elsevier Science Publishers B. V. 675–680

North, M. Tetrahedron Letters, 1996 37 1699–1702

Sakaki, J., Kobayashi, S., Sato, M. and Kaneko, C. Chem. Pharm. Bull., 1989 37 2952–2961

Servi, S. Synthesis, 1990 1–25

Shiu, H. S. and Rogers, P. L. Biotechnol. Bioeng., 1996 49 52–62

Ward, O. P. Can. J. Bot., 1995 73 S1043–S1048

What is claimed is:

1. A method of synthesis of a carbinol compound, comprising the step of subjecting the corresponding aromatic aldehyde to an acyloin condensation reaction mediated by a yeast in an organic solvent under non-fermenting conditions, in the presence of an aliphatic alcohol or aliphatic aldehyde, in which the reaction mixture comprises water sufficient to activate the yeast, but not sufficient to form a two phase system.

2. A method according to claim 1, in which the yeast is *Saccharomyces cerevisiae*.

3. A method according to claim 1, in which the yeast is of a strain specifically adapted to an organic solvent environment or for enhanced reduction efficiency.

4. A method according to claim 1, in which the yeast is active dried yeast.

5. A method according claim 4, in which the aliphatic alcohol or aliphatic aldehyde is ethanol or acetaldehyde respectively.

6. A method according to claim 5, in which the proportion of ethanol or acetaldehyde is 0.1 ml/g yeast.

7. A method according to claim 5, in which the aliphatic alcohol or aliphatic aldehyde is ethanol.

8. A method according to claim 1, in which the reaction is performed at ambient temperature.

9. A method according to claim 1, in which the reaction is performed at 16–24° C.

10. A method according to claim 9, in which the reaction is performed at 20° C.

11. A method according to claim 1, in which the reaction is performed at 0–10° C.

12. A method according to claim 1, wherein the organic solvent selected from the group consisting of petroleum ether, carbon tetrachloride, hexane, other hydrocarbons, diethyl ether, toluene, and benzene.

13. A method according to claim 1, wherein the organic solvent is petroleum ether.

14. A method according to claim 1, wherein the organic solvent is a mixed organic solvent system.

15. A method according to claim 14, in which the mixed organic solvent system is selected from the group consisting of 2-ethoxyethanol/diethyl ether, pyridine/carbon tetrachloride, chloroform/petroleum ether and ethyl acetate/toluene.

16. A method according to claim 15, in which the mixed organic solvent system comprises 1 to 30% v/v of a polar organic solvent added to a non-polar organic solvent.

17. A method according to claim 16, in which the mixed organic solvent system comprises 1 to 5% v/v of polar organic solvent added to a non-polar organic solvent.

18. A method according to claim 17, in which the polar organic solvent is selected from the group consisting of chloroform, dichloromethane, methyl ethyl ketone, and methyl isobutyl ketone.

19. A method according to claim 18, in which the reaction is performed in chloroform or dichloromethane in petroleum ether.

20. A method according to claim 1, in which the reaction mixture comprises water at a ratio of 0.6 to 1.2 ml water/g of yeast.

21. A method according to claim 1, in which the reaction is conversion of an optionally-substituted aromatic aldehyde to the corresponding acyloin compound by condensation with an optionally-substituted pyruvat compound.

22. A method according to claim 21, in which the aromatic aldehyde substituted with one or more groups selected from the group consisting of alkyl, aryl, halo, nitro, hydroxy, alkoxy, amino, carbonyl, thioxy or thioalkoxy substituted with alkyl, aryl, halo, nitro, hydroxy, alkoxy, amino, carbonyl, thioxy or thioalkoxy alkyl, aryl, halo, nitro, hydroxy, alkoxy, amino, carbonyl, thioxy and thioalkoxy.

23. A method according to claim 21, in which the reaction is conversion of benzaldehyde to phenylcetylcarbinol.

24. A method according to claim 21, in which the pyruvate compound is pyruvic acid.

25. A method according to claim 24, in which the reaction is performed at a pH of between 5 and 6.

26. A method according to claim 21, in which the pyruvate compound is sodium pyruvate.

27. A method according to claim 26, in which the reaction is performed at a pH of between 5 and 8.

28. A method according to claim 1, in which the reaction time is 12 to 24 hours.

29. A method of synthesis of a substituted carbinol compound, comprising the step of subjecting the corresponding substituted aromatic aldehyde to acyloin condensation mediated by a yeast in an organic solvent under non-fermenting conditions, in which the reaction mixture comprises water sufficient to activate the yeast but not sufficient to form a two phase system.

30. A method of synthesis of a substituted carbinol compound, comprising the step of subjecting the corresponding substituted aromatic aldehyde to acyloin condensation mediated by a yeast in an organic solvent under non-fermenting conditions, in which the reaction is performed at 0–10° C.

* * * * *

UNITED STATES PATENT AND TRADEMARK OFFICE
CERTIFICATE OF CORRECTION

PATENT NO. : 6,271,008 B1
DATED : August 7, 2001
INVENTOR(S) : Smallridge et al.

It is certified that error appears in the above-identified patent and that said Letters Patent is hereby corrected as shown below:

<u>Column 3,</u>
Line 54, change "0-52º" to -- 0-5º --.

<u>Column 5,</u>
Line 50, change "50º C" to -- 5º C --.

Signed and Sealed this

Second Day of July, 2002

Attest:

JAMES E. ROGAN
Attesting Officer    Director of the United States Patent and Trademark Office